United States Patent [19]

Bertholdt

[11] Patent Number: 5,114,854
[45] Date of Patent: May 19, 1992

[54] PROCESS OF EFFECTING A MICROINJECTION INTO LIVING CELLS

[75] Inventor: Günter Bertholdt, Mössingen, Fed. Rep. of Germany

[73] Assignee: Firma Eppendorf-Netheler-Hinz GmbH, Hamburg, Fed. Rep. of Germany

[21] Appl. No.: 312,960

[22] Filed: Feb. 21, 1989

[30] Foreign Application Priority Data

Mar. 15, 1988 [DE] Fed. Rep. of Germany ....... 3808531

[51] Int. Cl.$^5$ ............................................. C12N 15/89
[52] U.S. Cl. ........................... 435/240.1; 435/172.1; 435/287; 935/53; 935/85; 73/864.25
[58] Field of Search ....................... 435/30, 172.1, 287, 435/3, 292, 240.1; 935/53, 85; 350/529–533, 507; 73/864.23–864.25; 436/174; 364/413.01, 167.01; 359/368, 391–395

[56] References Cited

U.S. PATENT DOCUMENTS

| | | | |
|---|---|---|---|
| 4,532,205 | 7/1985 | Ansorge | 435/30 |
| 4,619,899 | 10/1986 | Nikitin et al. | 435/287 |
| 4,762,405 | 8/1988 | Inoue et al. | 350/510 |
| 4,907,158 | 3/1990 | Kettler et al. | 364/413.01 |

FOREIGN PATENT DOCUMENTS

| | | | |
|---|---|---|---|
| 0118473 | 6/1985 | Japan | 435/287 |
| 0675359 | 7/1979 | U.S.S.R. | 935/53 |
| 2022287 | 12/1979 | United Kingdom | |

OTHER PUBLICATIONS

"Micromanipulateurs steretaxigues dans le domaine chirurgical", Diaz et al., 8132 Revue Generale de l'Electricite, (1984), No. 11, Paris, France, pp. 747–751.

Primary Examiner—Robert J. Warden
Assistant Examiner—William H. Beisner
Attorney, Agent, or Firm—Toren, McGeady & Associates

[57] ABSTRACT

For a microinjection of liquids or suspensions of substances into living cells, a stage and a cannula, which is movably mounted and extends at an oblique angle relative to the stage, are arranged to be movable relative to each other, the cells being contained in a culture vessel on the stage, the tip of the cannula constitutes a pointer and is moved in a plane $z_1$, which is parallel to the stage and is disposed above the cells on the stage, the tip is moved to a position exactly over the location which is desired for an injection and thereafter, the cannula is moved away from the selected cell in the direction of the projection of the cannula on the plane and over a distance which depends on the angle between the cannula and the plane, the cannula is thus moved to a setback position, in which the axis of the cannula extends through the desired location, the cannula is then axially moved to puncture the cell and is subsequently reversed.

3 Claims, 5 Drawing Sheets

PROCESS OF EFFECTING A MICROINJECTION INTO LIVING CELLS

BACKGROUND OF THE INVENTION

1. Field of the Invention

This invention relates to a process of microinjecting liquids or suspensions of substances into living cells by means of a movably mounted cannula and a stage, wherein the cannula extends at an oblique angle to the stage, the cannula and the stage are adjustable relative to each other in two directions (X, Y) in a plane which is parallel to the stage, and the cannula is also movable in a direction Z, which is at right angles to the plane that is defined by the directions X and Y.

This invention relates also to an apparatus for carrying out the process, which apparatus comprises a holder for the cannula.

The term cannula includes also capillary tubes or microcapillary tubes.

2. Description of the Prior Art

In connection with such processes it has already been endeavored to achieve a certain mechanization in that a cannula which has been adjusted to be inclined from the vertical or to the stage is disposed above and aligned with a cell and is vertically lowered and this is accompanied by an observation under a microscope. In that operation, problems will arise in connection with the detection of the position of a cannula or capillary tube in the direction Z. It must also be taken into account that it is not always intended in microinjection technology to inject into the core of a cell even though an injection can be made into the core in other cases. In the known embodiments it is possible only to make a rough assessment of the location at which a puncture is to be made. The vertical downward movement involves the disadvantage that the cannula is forced into the cell by a movement having a considerable lateral component so that the membrane of the cell will be torn to form an elongate slit. This may result in irreversible damage to the cell membrane, i.e., to the cell as a whole. Besides, a cannula may break.

It is also known to use a stage which consists of the stage of a microscope and so to arrange a holder for the cannula that the tip of the cannula lies in the direction of observation and an exact observation is ensured in that the microscope is exactly focussed to the tip.

Such a stage which is a part of a microscope may consist of a known compound stage, which is adjustable relative to the objective. In that case, one cell or more cells of a large number of cells of a cell culture can be moved on the compound stage into the field of view of the microscope.

From that aspect a preferred embodiment of the invention is based on the assumption that numerous cells in a certain arrangement, e.g., in a special cell culture vessel, are provided on the compound stage and each cell can individually be positioned.

The known devices used for that purpose are highly expensive and under the control of a computer operate an automatically controllable compound stage to align one cell at a time with the cannula in accordance with a predetermined pattern.

Numerous means for controlling the cannula by computerized image-processing techniques could be conceived but would require a provision of relatively expensive additional means for controlling the movement of the microscope stage relative to the tip of the cannula.

SUMMARY OF THE INVENTION

It is an object of the invention so to improve a process and apparatus of the kind described first hereinbefore that an exact adjustment of a cannula relative to an individual cell at a time is facilitated and the cell can be punctured by an axial movement of the cannula.

In a process of the kind described first hereinbefore, that object is accomplished in accordance with the invention in that the tip of the cannula is used as a pointer, which is adjusted by a movement in a plane $z_1$ that is parallel to the stage and is disposed above the cell material to a position over a desired location at which an injection is to be made into a cell which is disposed on the stage, and the cannula is moved in said parallel plane away from said cell in the direction of the projection of the cannula on said plane and by a distance which depends on the angle between the cannula and said plane and is so long that the cannula is disposed at the end of the latter movement in a setback position, in which the axis of the cannula extends through the cell at the desired location for the injection, and the cannula is subsequently axially moved to puncture the cell and is arrested when the tip has arrived at the desired location for the injection.

Because the cannula is used as a pointer for directly marking the desired location of the intended puncture and the cannula is subsequently moved away from the cell, the microinjection can exactly be performed without an overstressing of the operator and the puncture can be effected by an axial movement and the positioning of the inclined cannula can visually be supervised.

When the cannula has manually been aligned and has then been moved away from the cell before the puncturing movement, that movement away from the cell initiates an automatic control action, which depends on the configuration of the arrangement and by which the cannula is first moved out of alignment with the cell to a setback position, from which it can axially be moved to puncture the cell. That process can be performed in a particularly desirable manner if the selected planes which are parallel to the stage are desirable for the movement of the cannula and for the definition of the extent of the puncturing movement. Special advantages will be afforded if a second plane which is parallel to the stage is defined above the stage at an elevation $z_0$ over the stage, said second plane substantially intersects the interior of each of the cells provided on the stage, and the axial puncturing movement of the cannula is arrested when the tip of the cannula has reached the plane $z_0$. In that case the cannula may extend at an angle of 45° to the plane of the stage and the extent of the setback movement may be equal to the distance between the planes $z_0$ and $z_1$.

In an apparatus which serves to carry out the process defined hereinbefore and comprises a holder for the cannula, the object set forth hereinbefore is accomplished in accordance with the invention in that the holder is adjustably mounted on an actuator, adjusting means are provided for defining an angle between the cannula and the holder, said actuator comprises at least two drive means, first of said drive means are operable to move the holder in one direction in said one plane which is parallel to the associated stage, second of said drive means are operable to move the holder in a direction which is at right angles to said plane, guide means are provided between the holder and the actuator and extend in the directions of movement which can be imparted by said at least two drive means, said at least two drive means are interposed between said holder and a base of the actuator, and the holder is guided by said guide means for a movement relative to said base.

Such an apparatus may be provided in any of various designs. If the actuator of the apparatus is provided in association with a stage which constitutes a compound stage for movements in the directions X, Y in a plane, it will be sufficient to provide in the actuator only one first drive means for the operation stated and one second drive means for imparting a movement in the direction Z. In that case the cannula may be adjusted relative to a cell by a movement by which the compound stage and the cell provided thereon are displaced.

In preferred embodiments, however, the actuator comprises two first drive means for imparting movements in the directions X, Y in said one plane. The guide means are associated with the drive means and may be constituted by undercut tracks and/or rails, as is known, e.g., from machine tools.

The actuator is in itself a special device for accomplishing the object set forth. In a desirable embodiment the actuator is provided with locating means, e.g., clamping means, for effecting a rigid connection to a stage. In that case the actuator may subsequently be attached to a stage, which may consist of a microscope stage or a stage of a different viewing device. In that case said drive means are not identical to the drive means associated with a compound stage of a microscope but they desirably have identical drive means for imparting movements in the directions X, Y in the plane of the compound stage. In that case the cannula tip that is used as a pointer can be adjusted as desired to a position over a cell which has been moved into the field of view of the microscope under the condenser.

In a suitable embodiment the actuator has a base that is rigid with a stage.

Further desirable features of the invention are defined in the claims.

DETAILED DESCRIPTION OF THE PREFERRED EMBODIMENTS

Figure 1:
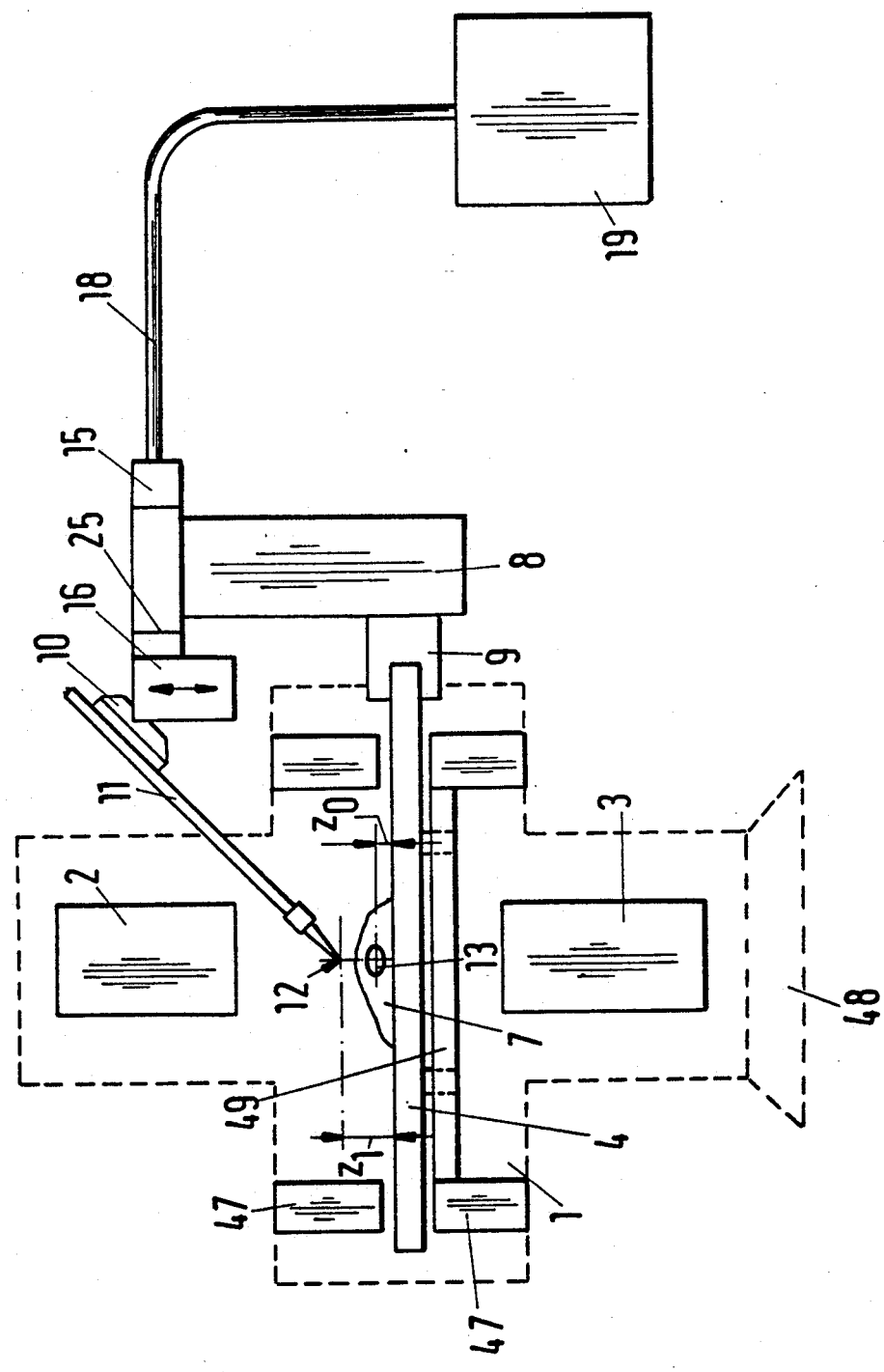
FIG. 1 is a diagrammatic side elevation showing an apparatus in accordance with the invention.

Illustrative embodiments of the invention will now be described more in detail with reference to the drawing.

In FIG. 1, a microscope 1 is diagrammatically indicated by a dotted line and comprises a condenser 2 and an objective 3. This is an inverted microscope.

A compound stage 4 is movably mounted in known manner in that microscope. The mounting means are diagrammatically indicated at 47. The microscope 1 is mounted on a stand 48.

Figure 2:
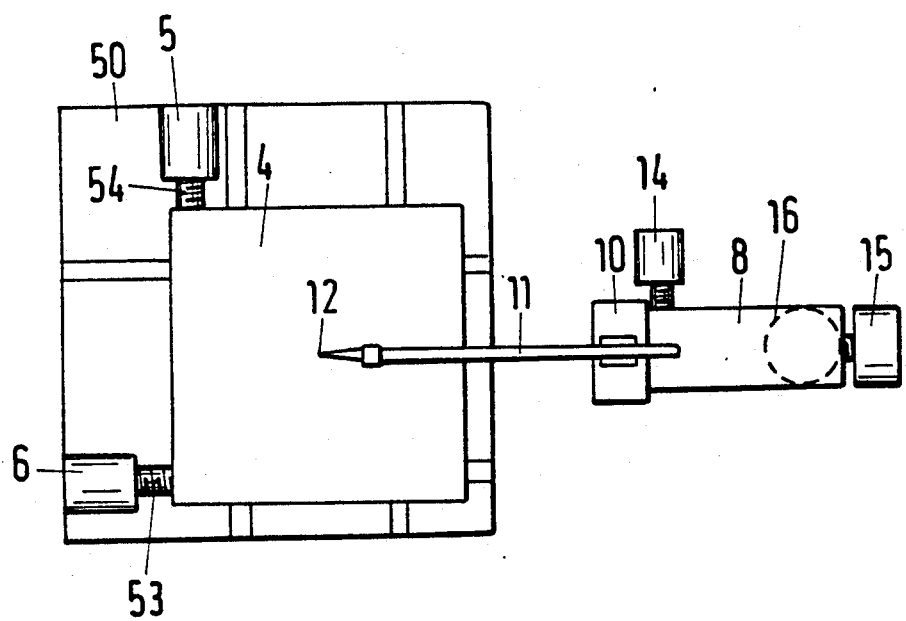
FIG. 2 is a fragmentary diagrammatic top plan view showing a part of the apparatus in accordance with FIG. 1 but provided with additional parts.

The compound stage 4 is adjustable relative to the line of view between 2 and 3 by two first drive means 5, 6 (FIG. 2). The mounting means 47 include guides 49 for the compound stage. Said guides 49 may consist in known manner of crossing rails.

The two first drive means comprise, for instance, spindles 53, 54 for moving the compound stage 4 along the guides 49. Said first drive means 5, 6 also comprise two reversible motors and are mounted in fixed positions in the stand of the microscope 1. The spindles 53, 54 may also constitute the carrying means.

By the adjustment that is effected by the two first drive means 5, 6 a cell 7, which in addition to numerous other cells is provided on the compound stage 4, is moved into the line of view between the condenser 2 and the objective 3.

An actuator 8 is mounted on the compound stage and may be integral with the compound stage or may rigidly be connected to the compound stage 4 by mounting means 9.

A holder 10 which holds a cannula 11 is movably mounted on the actuator. That cannula is inclined to the compound stage, desirably at an angle of 45°. The cannula 11 has a tip 12, which serves also as a pointer and by drive means can be adjusted to a position over the core 13 of the selected cell 7.

Said drive means for aligning the pointer that is constituted by the tip with the cell may be constituted by the drive means for the compound stage or by the second drive means 14, 15, 16 of the actuator 8 which serve to operate the holder 10. Said two drives may be combined with each other.

In a basic embodiment the pointer which is constituted by the tip of the cannula is normally in a predetermined position and the compound stage 4 is adjusted during an observation through the microscope to such a position that the pointer is disposed over a cell core 13.

The subsequent movements are imparted to the cannula by the second drive means 14, 15, 16.

FIG. 1 shows one of the second drive means 16, which serves for the adjustment in height, and another second drive means 15 for imparting to the cannula 11 a movement which is parallel to the stage 4 and in the direction of the projection of the cannula 11 on a plane that is parallel to the stage 4.

The actuator 8, the holder 10 and the cannula 11 are diagrammatically shown in FIG. 2. Two second drive means 14, 15 are provided for imparting movements at right angles to each other in the x-y plane, which is parallel to the plane of the stage 4. The first drive means 5, 6 and the second drive means 14, 15 can be used to adjust the tip 12 of the cannula 11 relative to a cell which is provided on the compound stage. If only the drive means 5, 6 are used for that purpose, it will be sufficient in the illustrated embodiment to provide in the actuator 8 as second drive means only one drive means 15 for imparting to the cannula 11 a movement in the direction of the projection of the cannula and second drive means 16 for imparting a movement in the direction Z at right angles to the x-y plane which is defined by the drives 14, 15.

The supplemental matter which is shown in FIG. 2 in addition to FIG. 1 comprises the second drive means 14, which are included in the actuator 8 and serve to move the cannula 11 in the x-y plane. The second drive means 14, 15, 16 suitably consist also of reversible electric motors, which are connected in circuit in conventional manner and provided with reversing switch means.

It will be understood that an interposed carriage 50 is provided between the cross-slide that is provided with the drive means 14, on the one hand, and the part which is adjustable in height. Said interposed carriage 50 may be provided on various sides with guide means which extend at right angles to each other.

Special guide means for guiding the holder 10 relative to the actuator 8 are not shown in FIG. 1 and may consist in the usual manner of undercut tracks, rails or the like, just as the slide tracks for the compound stage and the other slide tracks which will be described with reference to FIG. 4.

Besides, the holder 10 is connected to a merely diagrammatically indicated adjusting device 25 for adjusting the angle between the cannula 11 and the compound stage 4. That adjusting device 25 is shown more clearly in FIG. 4.

In the position shown in FIG. 1 the tip 12 of the cannula 11 has an elevation $z_1$ over the compund stage 4. The plane $z_1$ is disposed above the cell 7. Another variable is defined by a plane $z_0$, which is shown in FIG. 1 and is also disposed over the compound stage 4 but intersects the cell core 13. It is apparent that the tip 12 of the cannula 11 is movable in a plane having the elevation $z_1$ to a position over the cell core 13 and this can be observed through the microscope.

In FIG. 1, a supply line 18 and a supply vessel 19 for supplying the substance to be examined to the cannula are merely formally shown. A function line 18 is indicated, which serves to transmit control signals for the second drive means and possibly also to the adjusting device 25.

As a result of an observation or of experience, a plane which is parallel to the compound stage 4, i.e., to the supporting surface of said stage, is adjusted to such an elevation that said plane intersects the core 13 of a cell disposed on that supporting surface. This adjustment is effected to permit the process to be carried out and the apparatus to be operated. When the cannula 11 has been moved to a position in which its tip 12 has arrived at the center of the cell core 13, i.e., has reached the plane thus defined, said movement of the cannula is arrested and a setback movement is initiated. This will be explained more in detail hereinafter, particularly with reference to FIG. 3.

Figure 3A:
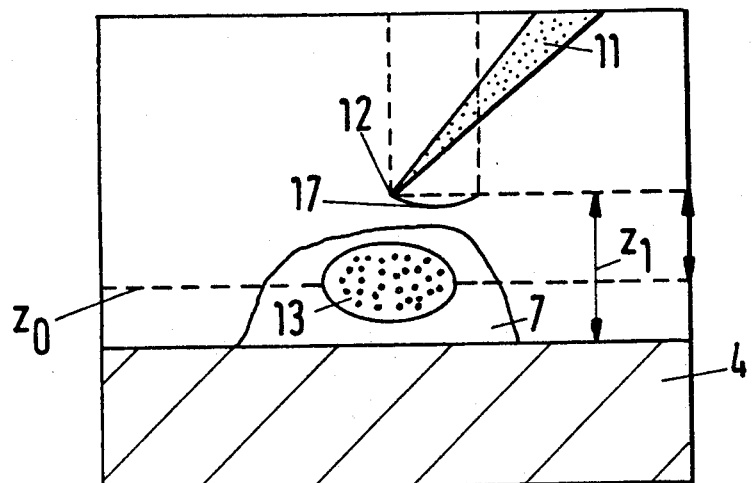
FIGS. 3a) to 3c) are three greatly enlarged diagrammatic side elevations for explaining the adjustment of the cannula.

Each of FIGS. 3a) to 3c) shows a portion of the compound stage 4 with the cell 7 having the core 13. The tip 12 of the cannula 11 is disposed over the cell core in a plane which is spaced a distance $z_1$ over the supporting surface of the compound stage 4. That plane will be designated $z_1$.

FIGS. 3a) to 3c) show also a plane $z_0$ which intersects the cell core 13.

Figure 5:
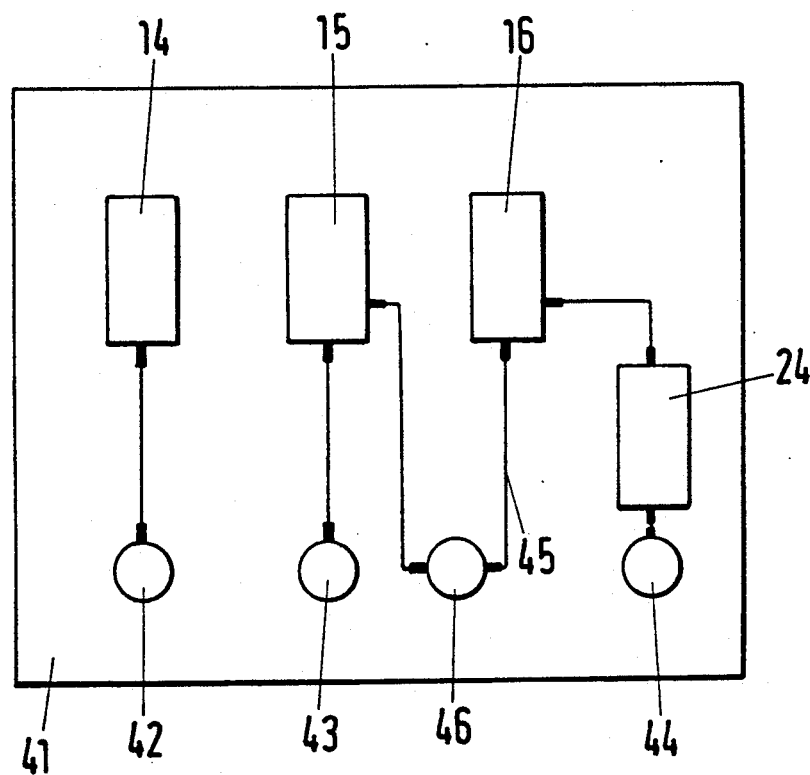
FIG. 5 is a basic circuit diagram for the actuator.

FIG. 3a) shows the tip 12 of the cannula 11 in a position over the cell core 13. The tip 12 of the cannula 11 has been observed in accordance with FIG. 1 as it was adjusted to that position. After that adjustment the holder 10 shown in FIG. 1 and the cannula 11 are moved in a direction which is parallel to the plane of the compound stage 4 by a distance 17 in a given direction, e.g., in the direction X, to a position in which the tip 12' will axially puncture the cell core 13 when the cannula 11 is axially moved by a simultaneous operation, e.g., of the drive means 15 and 16 (FIG. 3c). The setback movement is imparted by one of the drive motors 14 and 15 in dependence on the association. The puncturing movement is imparted to the cannula by a simultaneous operation of the drive means 15, 16 (FIG. 5).

That puncturing movement is limited in that the drive means for imparting an axial forward movement are deenergized as soon as the tip 12 has arrived at the plane $z_0$, as has been explained hereinbefore. That limit has been stored in the control unit 35 (FIG. 4), which causes the control device 37 to initiate the movements.

It is also possible to effect a reversal and another adjusting movement by which the tip 12 used as a pointer is moved in a plane $z_1$ relative to the compound stage 4 by the drive means 14, 15 to a position at the vertical projection of another cell core 13 on the compound stage 4.

Figure 3B:
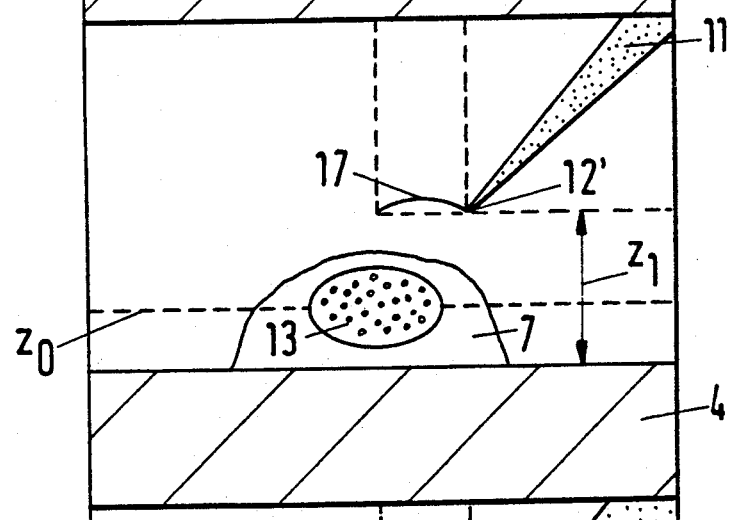
Figure 3C:
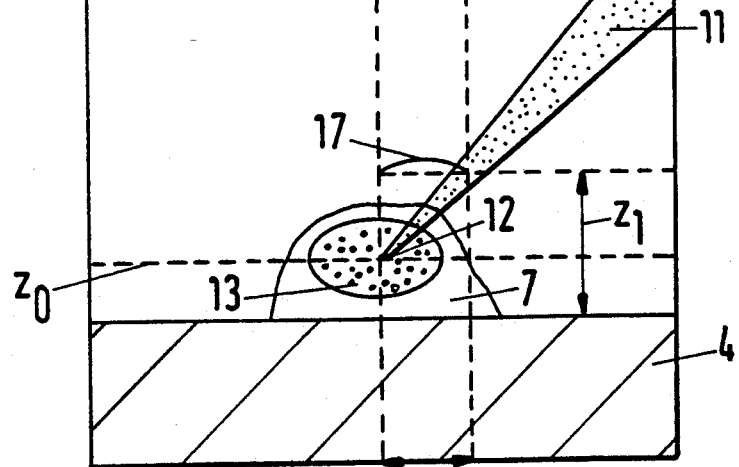

FIG. 3 shows a cannula which extends at an angle of 45° to the compound stage. In that embodiment the distance between the planes $z_1$ and $z_0$ equals the distance 17, as is particularly distinctly apparent from FIG. 3). In that case the cannula 11 will be moved at 45° to the table 4 by the simultaneously imparted movements in the vertical and horizontal d rections and will axially puncture the cell core 13.

Figure 4:
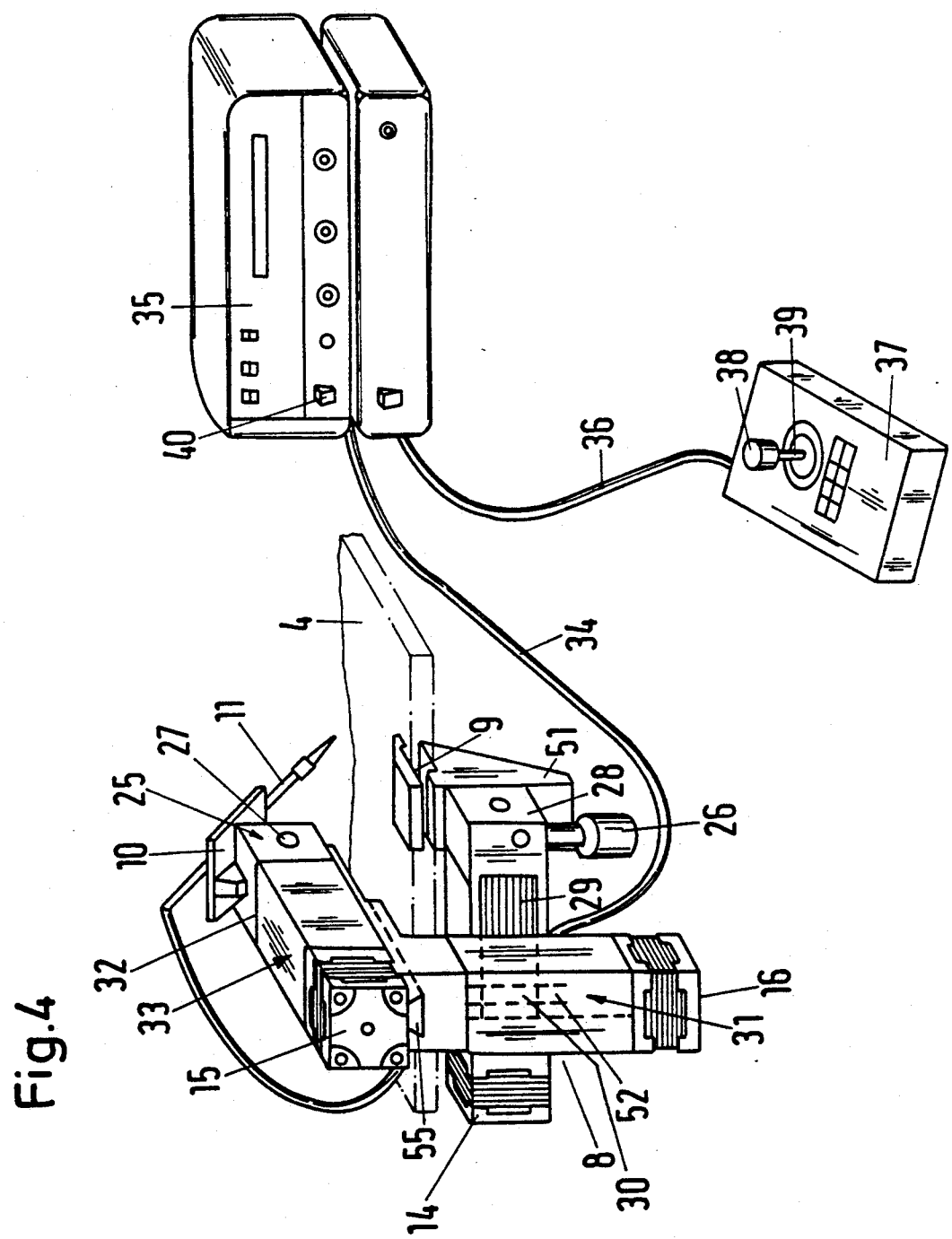
FIG. 4 is a diagrammatic fragmentary perspective view showing an apparatus.

FIG. 4 shows a stage 4, e.g., of a microscope. That stage carries the actuator 8, which is connected to the stage 4 by a mounting device 9, which can be clamped to the stage 4, e.g., by a setting head 26.

That stage 4 may also consist of an independent unit provided with the actuator 8 and the associated parts.

The actuator 8 comprises three second drive means 14, 15, 16 for imparting the movements which have been described. A practical embodiment is shown in FIG. 4. An angular adjustment can be imparted to the holder 10 and the cannula 11 by the adjusting device 25, which is provided for that purpose with an adjusting knob 27.

A guiding subassembly 28 is secured to the base 51 of the actuator 8 and comprises track rails 29, which extend parallel to the stage and serve to guide a carriage 30, which is indicated by dotted lines and can be laterally displaced by the second drive means 14 in parallel to the guiding subassembly.

The carriage 30 is provided with vertical track rail arrays 52 for a guiding subassembly 31, which is associated with the second drive means 16, which serve to impart a movement in the direction Z.

A cantilever which extends at right angles to the guiding subassembly 31 is carried by the latter and is provided with a diagrammatically indicated rail track 55 for a third subassembly 33, which is movable in a direction which is parallel to the plane of the stage but at right angles to the direction of movement that is defined by the guiding subassembly 28. For that purpose the third guiding subassembly is moved by the second guide means 15 as is shown in FIG. 2.

A simple embodiment of the actuator 8 is shown in FIG. 4 and is connected by the control line 34 to control units 35, which serve to control a microscope or the movement of a compound stage 4. Said control units comprise also the switch means for controlling the drive means or their motors. A control device 37 is connected by a functional link 36 and is provided with a hand lever 38, which is movable to different angular positions to initiate a movement in the direction X, Y. Such joystick controls are known. A movement in the direction Z can be initiated by a rotation or depression of an element that is provided on the control handle 39. A lever 40 may be adjustable to determine whether the drive means associated with the compound stage 4 or those included in the actuator 8 will be operated.

As is apparent from the circuit diagram in FIG. 5, the actuator 8 has associated with it a control subassembly 41, which accommodates the three second drive means 14, 15, 16 or, if these are spatially separated, as is shown in FIG. 4, the correspondingly number switching means, which in that case are connected by control lines to the drive means. This is diagrammatically indicated by the combined control line 34.

It is apparent that actuating levers 42, 43 are associated with the second drive means 14, 15 for imparting movements in the directions X, Y. Said levers 42, 43 permit said second drive means 14, 15 to be separately energized. In the embodiment shown in FIG. 4 said actuating levers are accommodated in the control device 37 and associated with the control handle 39. That remark is also applicable to the part 44.

The second drive means 16 for imparting a movement in the direction Z is connected to a measuring device 24, which comprises an adjusting lever 44 for adjusting the distance between the planes $z_0$ and $z_1$. The second drive means 16 is operable in dependence on that adjustment.

In that embodiment, the second drive means 15, 16 are interconnected by a control loop 45, which is provided with control device 46, which is manually operable to disconnect all other individual power lines leading to the drive means 15 and 16 and for energizing the second drive means 15 and 16 for an operation at the same speed only when the cannula is arranged at an angle of 45° in view of the explanations furnished hereinbefore. Particularly the second drive means 15, 16 are reversible because when the tip 12 of the cannula 11 has arrived at the plane $z_0$ the measuring device 24 will automatically effect a reversal and a return movement of the tip 12 of the cannula to the plane $z_1$.

In the embodiment of the actuator 8 shown in FIG. 4 the guiding subassemblies 28, 31 and 33 can be moved along the associated rails by respective rack-and-pinion drives, the pinion of which is driven by one of the drive means.

I claim:

1. A process for placing a cannula at a desired location within a living cell positioned on a stage, comprising the steps of:

providing a stage with living cells positioned thereon;
    providing a movably supported cannula which has an axis along the length thereof and a tip at the end thereof, said tip constituting a pointer, said cannula being adjustably connected to said stage so that said tip is proximate to said stage and said axis forms an acute angle with respect to said stage, said cannula and said stage being movable relative to one another along two perpendicular axes (X, Y) in a plane that is parallel to said stage, said cannula also being movable along a vertical axis (Z) which is perpendicular to said parallel plane;
    moving said cannula in a first plane ($Z_1$) above a cell and parallel to said stage so that said tip points to a desired location within the cell, wherein said tip is spaced from said desired location along said vertical axis which intersects said desired location;
    imparting a setback movement to said cannula from said pointing location, as a function of said acute angle and in a direction of a projection of said cannula on said parallel plane for a distance which is sufficient so that said cannula at an end of said setback movement is in a position to intersect said desired location when moved in a direction along said axis of said cannula towards the cell;
    puncturing the cell by moving said cannula from said setback position in a direction along said axis of said cannula;
    arresting said puncturing movement when said tip has intersected said desired location.

2. A process according to claim 1, further including;
    defining a second parallel plane ($Z_0$) which is parallel to said stage and extends through said desired location within each cell positioned on said stage, and arresting said puncturing movement when said tip has intersected said second parallel plane.

3. A process according to claim 2, wherein said acute angle is 45 degrees and the distance of the setback movement is equal to the distance between said first plane and said second plane.

* * * * *